United States Patent
Berland et al.

(10) Patent No.: US 9,168,185 B2
(45) Date of Patent: Oct. 27, 2015

(54) ABSORBENT ARTICLE COMPRISING A TEMPERATURE SENSOR AND A TEMPERATURE CHANGE MATERIAL

(75) Inventors: Carolyn Berland, Molndal (SE); Tomas Karlson, Savedalen (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/366,820

(22) PCT Filed: Dec. 22, 2011

(86) PCT No.: PCT/EP2011/073803
§ 371 (c)(1),
(2), (4) Date: Jun. 19, 2014

(87) PCT Pub. No.: WO2013/091707
PCT Pub. Date: Jun. 27, 2013

(65) Prior Publication Data
US 2014/0350502 A1    Nov. 27, 2014

(51) Int. Cl.
*A61F 13/42*   (2006.01)

(52) U.S. Cl.
CPC ............ *A61F 13/42* (2013.01); *A61F 2013/424* (2013.01)

(58) Field of Classification Search
CPC ............ A61F 13/42; A61F 2013/00944; A61F 2013/00953; A61F 2013/421; A61F 2013/424; A61F 2013/426
USPC ........................................................ 604/361
See application file for complete search history.

(56) References Cited

U.S. PATENT DOCUMENTS

| 5,649,914 A * | 7/1997 | Glaug et al. .................. 604/361 |
| 2006/0069363 A1 | 3/2006 | Weber et al. |
| 2006/0142713 A1 | 6/2006 | Long et al. |

(Continued)

FOREIGN PATENT DOCUMENTS

| CN | 101389298 A | 3/2009 |
| CN | 101918847 A | 12/2010 |

(Continued)

OTHER PUBLICATIONS

Office Action dated Nov. 4, 2014 issued in corresponding Chinese patent application No. 201180075609.X (with English translation thereof) (18 pages).

*Primary Examiner* — Lynne Anderson
*Assistant Examiner* — Kathryn E Ditmer
(74) *Attorney, Agent, or Firm* — Drinker Biddle & Reath LLP (57) ABSTRACT

An absorbent article including a temperature sensor, and at least one temperature change material arranged such that it is capable of affecting a temperature change due to a supply of excrement, and such that said temperature sensor is capable of being responsive to said affected temperature change. Also disclosed is a system for detecting a supply of excrement into an absorbent article, the system including an absorbent article being arranged to generate an output signal representative of the temperature, and a processing unit adapted to process an output signal generated by the temperature sensor. The processing unit is adapted to determine a change of temperature, wherein said change of temperature is affected by the temperature change material, and to detect a supply of excrement into the absorbent article based on the change of temperature.

25 Claims, 8 Drawing Sheets

(56) References Cited

U.S. PATENT DOCUMENTS

| | | | |
|---|---|---|---|
| 2008/0045913 A1* | 2/2008 | Johnson et al. | 604/361 |
| 2009/0157025 A1* | 6/2009 | Song et al. | 604/361 |
| 2009/0287172 A1 | 11/2009 | Lowe | |
| 2010/0160882 A1 | 6/2010 | Lowe | |
| 2012/0310192 A1* | 12/2012 | Suzuki et al. | 604/361 |

FOREIGN PATENT DOCUMENTS

| | | |
|---|---|---|
| JP | 2010-194277 A | 9/2010 |
| KR | 2010-0091612 A | 8/2010 |
| WO | WO-2006/119523 A1 | 11/2006 |
| WO | WO-2007/128038 A1 | 11/2007 |
| WO | WO 2009/077885 | 6/2009 |
| WO | WO 2011/078325 A1 | 6/2011 |

* cited by examiner

ABSORBENT ARTICLE COMPRISING A TEMPERATURE SENSOR AND A TEMPERATURE CHANGE MATERIAL

CROSS-REFERENCE TO PRIOR APPLICATION

This application is a §371 National Stage Application of PCT International Application No. PCT/EP2011/073803 filed Dec. 22, 2011, which is incorporated herein in its entirety.

TECHNICAL FIELD

Generally, the disclosure relates to a system and method for detecting a supply of excrement, such as feces and urine, especially liquid excrements. In particular, the disclosure relates to an absorbent article including a temperature sensor suitable for such a system and method. Further, the disclosure relates to a kit including an absorbent article and a temperature sensor.

TECHNICAL BACKGROUND

Systems for detecting and discriminating between supply of urine and supply of feces are known in the art. For instance, WO 2006/119523 discloses a health care system comprising a sensor unit arranged in a diaper and a processing unit. The sensor unit measures temperature and humidity at short intervals. Based on the measured data the processing unit detects and discriminates between feces and urine.

However, a drawback of the system disclosed in WO 2006/119523 can be that temperature sensors are generally vulnerable to false alarms. In addition, there is a risk of non-detection when the difference between the temperature of the core of a dry, or a partly wet, diaper and the temperature of the urine, feces, or other excrement is low.

Therefore, there is a need for improved systems that at least alleviates the problems of prior art systems and offers accurate detection even though the wearer of the absorbent article, such as a diaper, is in such a warm environment, such that the temperature of the core of a dry, or a partly wet, diaper and the temperature of the urine, feces, or other excrement is low as under a quilt in a bed or in a warm climate.

SUMMARY

The present disclosure is based on an insight that a difference between a temperature of a core of an absorbent article and a temperature of urine or feces supplied into the absorbent article is often quite small, and therefore the difference can be difficult to detect. Thus, it is desired to obviate or at least alleviate the above mentioned problems.

The absorbent article includes a temperature sensor, and at least one temperature change material arranged such that it is capable of affecting a temperature change due to a supply of excrement, and such that said temperature sensor is capable of being responsive to said affected temperature change.

Herein, absorbent article refers to an adult incontinence product, a baby or toddler diapers, sanitary towels, liners or other known absorbent articles. Further, a temperature sensor is intended to mean a sensor that is adapted to react/be responsive to and/or measure a change of temperature. The temperature sensor can be integrated into said absorbent article or be separate from said absorbent article and arranged in the absorbent article with suitable fastening means such that it is capable of being responsive to said affected temperature change. A supply of excrement is intended to mean supply of urine, feces, menstruation liquids, etc. Still further, wordings supply of excrement and a supply of excrement are used alternately in this application having the intended meaning described above. A temperature change material is intended to mean a material that can be activated by liquid, i.e. water, in excrement, such as urine or feces, which is brought into contact with the temperature change material, for changing the temperature of the temperature change material. Herein, activated is intended to mean that the temperature change material gives rise to a temperature change, by being solved into water, by reacting with water, by reacting when dissolved etc. Thus, the temperature change material can be any material that affects and changes the temperature within the absorbent article due to supply of liquid. The temperature change material can be an exothermic material or an endothermic material. Alternatively, the absorbent article may include a combination of different temperature change materials. Further, affecting a temperature change is intended to mean either that an increase in temperature is amplified, such that the increase is higher than what would be without a temperature change material, or that instead of an increase there will be a decrease in temperature.

Due to the temperature change material, a temperature change within a core/inside of an absorbent article due to a supply of excrement, such as feces or urine, having a different temperature than the dry inside/core, can be greater than without temperature change material. However, depending on the position of the temperature change material in relation to the side of the article that is facing the crotch region of a user, the amount of liquid of feces reacting with or coming in contact with and thus activating the temperature change material will vary. If all the liquid of the feces is absorbed by the core before reaching the temperature change material, there will be no reaction with the fluid of feces and the temperature change material. Thus, the vertical position of the temperature sensor affects the difference of the detected signal for urine and feces, respectively. Herein, vertical is intended to mean in a vertical direction when an absorbent article is in use or laid out flat with the top sheet facing up. By arranging the temperature sensor near a back sheet of the absorbent article, the difference between the respective detected signals will be greater, while by arranging the temperature sensor near a top sheet of the absorbent article the difference between the respective detected signals will be slighter.

If the temperature change material is an endothermic material, the temperature change will be a decrease in temperature, while if the temperature change material is an exothermic material, the temperature change will be an amplified increase in temperature. Therefore, if a temperature change material is arranged in an absorbent article, the temperature sensor can detect a more distinct change of temperature than without a temperature change material, that is, with a temperature sensor alone. Herein, more distinct can be either a greater detectable signal or a signal of different type, i.e. a decrease instead of an increase. Consequently, the temperature change material will result in more accurate detection of a supply of excrement, and especially a supply of urine or other liquid. Therefore, even if the temperature difference between the temperature in a dry core of an absorbent article and the excrement is quite small, the supply of excrement can be more accurately detected than without a temperature change material.

Further, urine and feces have different temperature characteristics. Generally, urine is associated with a greater and faster temperature increase per unit of time than feces. In use, when excrement is supplied to the absorbent article, the temperature change material arranged adjacent to the temperature sensor will be activated by the supplied excrement and affect the difference between the temperature characteristics of urine and feces. Consequently, more accurate discrimination between supply of urine and supply of feces can also be obtained.

According to at least one example embodiment, the temperature change material is arranged adjacent to the temperature sensor. Herein, adjacent is intended to mean in the absolute vicinity of or located near to the temperature sensor.

According to at least one example embodiment, a distance between the temperature sensor and the temperature change material is 0-10 mm, 0-5 mm, or 0-2 mm.

If the temperature change material is arranged close to the temperature sensor a smaller amount of temperature change material is needed, resulting in a more cost effective absorbent article.

According to at least one example embodiment, said temperature change material is arranged in physical contact with at least a portion of said temperature sensor.

"In physical contact" is intended to mean that the temperature change material is coated on at least a portion of the temperature sensor or arranged adjacent to the temperature sensor in its absolute vicinity. Alternatively, the temperature change material can be at least partially enclosing the temperature sensor. Further, the temperature change material can be arranged continuously along a portion of the temperature sensor, or in discrete portions spaced apart from each other.

If the temperature change material is arranged in physical contact with the temperature sensor, a smaller amount of temperature change material is required for obtaining a desired influence of the change of temperature. Consequently, more accurate detection of a supply of excrement and/or discrimination between supply of urine and supply of feces can be provided for using a smaller quantity of temperature change material. Thus, such an absorbent article will be more cost effective to produce. In addition, a smaller quantity of temperature change material arranged adjacent to the temperature sensor affects the fluid in the proximity of the sensor, while the fluid in the rest of the article can stabilize the temperature changes relatively fast and the article will be more comfortable for the user. Further, a smaller quantity of temperature change material results in that the temperature will not change as much and fast as for a greater quantity. Therefore, the risk of discomfort for the user of the absorbent article due to fast temperature changes is decreased.

According to at least one example embodiment, the temperature sensor is reusable and arrangeable in the absorbent article such that the temperature sensor is capable of being responsive to the affected temperature change.

Suitably, such a reusable sensor is detachable from said absorbent article after use. Since a reusable temperature sensor allows for using one temperature sensor with a plurality of absorbent articles, an absorbent article with a reusable temperature sensor will be cheaper. Suitably, the absorbent article includes an indication, for instance in form of print or holes, for a correct position of the temperature sensor, ensuring that the temperature sensor will be arranged such that it is of being responsive to the temperature change affected by the temperature change material.

According to at least one example embodiment, the absorbent article further includes a sensor retaining portion adapted to receive and retain the temperature sensor, wherein said sensor retaining portion is arranged such that a temperature sensor inserted into said sensor retaining portion is capable of being responsive to the affected temperature change.

The sensor retaining portion can be a channel or recess adjacent to the core of the absorbent article in communication with a through hole in the back sheet or the top sheet of the absorbent article through which the temperature sensor can be inserted. Alternatively, the sensor retaining means can be a pocket, or other suitable retaining means, arranged on the back sheet or top sheet of the absorbent article. However, such sensor retaining means is arranged such that it will not increase the risk for leakage or inconvenience for the user.

According to at least one example embodiment, said temperature change material is arranged in at least two discrete portions spaced apart from each other.

According to at least one example embodiment, said temperature sensor is adapted to generate an electric or visual output signal, and, in particular embodiments, an electric signal.

According to at least one example embodiment, an amount of said temperature change material corresponds to a change in temperature, which said temperature sensor is capable of being responsive to.

According to at least one example embodiment, said absorbent article includes a back sheet, a top sheet and a core arranged between the back sheet and the top sheet, wherein the temperature sensor and the temperature change material are arranged adjacent to a back sheet of the absorbent article in contact with the absorbent core, wherein said temperature sensor is arranged substantially longitudinally along the absorbent article.

That is, a longitudinal extension of the temperature sensor is arranged substantially longitudinally in the absorbent article.

According to at least one example embodiment, said temperature change material is at least partly covered by a water soluble polymer.

Herein, covered is intended to mean covered at least on one side, totally encapsulated, or combinations of these. Such a cover of a water soluble polymer is advantageous, since generally temperature change materials are hygroscopic and therefore need to be protected against moisture before use of the absorbent article. In addition, such an encapsulation can also protect the material against small amounts of humidity due to perspiration during use.

According to at least one example embodiment, the temperature sensor and said temperature change material are arranged on a carrier material.

According to at least one example embodiment, the amount of said temperature change material corresponds to a change in enthalpy, $\Delta H$, of $\pm(0.1\text{-}500)$ J, $\pm(0.4\text{-}400)$ J, or $\pm(1\text{-}250)$ J, for each supply of excrement.

According to at least one example embodiment, the affected temperature change, $\Delta T$, equals to a factor, C, times said temperature change due to a supply of excrement, $C*\Delta t$, wherein C is either a positive or negative. That is, $\Delta T = C*\Delta t$.

For an endothermic material temperature change material the factor C is negative. Further, for an exothermic material temperature change material the factor C is positive.

The temperature sensor and said temperature change material can be arranged on the substrate or carrier material by printing or other suitable method. Suitably, also the water soluble polymer is arranged on said carrier material by printing or using another suitable method.

According to at least one example embodiment, said temperature change material is an endothermic material.

An endothermic material is advantageous, since there is no risk that such a material gives rise to an uncomfortable burning sensation for a person wearing the absorbent article, due to activation of the temperature change material.

According to at least one example embodiment, the temperature change material is an exothermic material.

An exothermic material is advantageous, since such a material gives a rise in temperature which is added to the temperature rise due to a supply of excrement. Therefore, there will be no risk of the temperature decrease due to presence of an endotherm material to be equal to the temperature rise due to a supply of excrement. Such equality would result in a detected constant temperature and the temperature change due to a supply of excrement could not be detected in such a case. Instead, the equality would lead to misdetection of a supply of excrement.

According to at least one example embodiment, the amount of said temperature change material corresponds to a positive affected temperature change, $\Delta T$, when activated by water, of at least 2° C., at least 5° C., or at least 10° C.

Herein, water is intended to mean water as a part of some kind of composition, water is not intended to mean pure water. All kinds of excrement includes water which can activate the temperature change material. Thus, the water for activating the temperature change material is comprised in the excrement supplied into the absorbent article. Suitably, for avoiding a risk that a user of the absorbent article feels a burning sensation, the positive temperature change, $\Delta T$, is not greater than 20° C. That is, the positive temperature change, $\Delta T$, is 2-20° C., 5-20° C., or 10-20° C.

According to at least one example embodiment, the amount of said temperature change material corresponds to a change in enthalpy $\Delta H$, of ±0.4-150 J, or ±1-50 J, for each supply of excrement.

According to at least one example embodiment, said temperature change material includes a chemical which is activated in contact with water, such as a metal hydroxide or an iron compound.

Herein, activated is intended to mean that the temperature change material gives rise to a temperature change, by being solved into water, by reacting with water, by reacting when dissolved etc.

According to at least one example embodiment, said temperature change material includes a mixture of chemical which react when dissolved into water, such as a weak acid and a base, or an organic acid and a bicarbonate, or citric acid and sodium bicarbonate, $NaHCO_3$.

According to at least one example embodiment, said temperature change material includes a metal chloride, such as magnesium chloride, potassium chloride, or calcium chloride.

According to at least one example embodiment, said temperature change material includes an ammonium salt, such as ammonium chloride.

A second aspect relates to a system for detecting a supply of excrement. The system includes an absorbent article according to the first aspect, being arranged to generate an output signal representative of the temperature, and a processing unit adapted to process an output signal generated by the temperature sensor. The processing unit is adapted to determine a change of temperature, wherein said change of temperature is affected by the temperature change material, and detect a supply of excrement into said absorbent article based on said change of temperature, whereby the supply of excrement is associated with a change of temperature.

Such a system is advantageous since it allows for more accurate detection of a supply of excrement, especially a supply of urine or liquid, even though the temperature difference between the core of the absorbent article and the excrement supplied into the absorbent article is relatively small. Other advantages with such a system are similar to the advantages of the first aspect described above.

According to at least one example embodiment, said processing unit is further adapted to discriminate between a supply of excrement in form of urine and a supply of excrement in form of feces based on said change of temperature.

A third aspect relates to method of detecting and discriminating between supply of urine and supply of feces into an absorbent article according to the first aspect. The method includes the steps of determining a change of temperature, wherein said change of temperature is affected by the temperature change material; and detecting a supply of excrement based on said change of temperature.

Such a system is advantageous since it allows for more accurate detection of a supply of excrement, especially a supply of urine or liquid, even though the temperature difference between the core of the absorbent article and the excrement supplied into the absorbent article is relatively small. Other advantages with such a system are similar to the advantages of the first aspect described above.

According to at least one example embodiment, the method includes the step of discriminating between a supply of excrement in form of urine and a supply of excrement in form of feces based on said change of temperature.

A fourth aspect relates to a kit including an absorbent article and a temperature sensor, wherein said absorbent article includes at least one temperature change material arranged such that it is capable of affecting a temperature change due to a supply of excrement, and such that said temperature sensor is capable of being responsive to said affected temperature change when arranged in contact with said absorbent article.

Herein, in contact with is intended to mean any type of contact which will result in the desired effect, i.e. in that the temperature sensor is capable of being responsive to said affected temperature change. That is, the temperature sensor can be inserted into said absorbent article by means known by a person skilled in the art or attached to a back sheet or a top sheet of the absorbent article using suitable retaining means. Still alternatively, the absorbent article can include sensor retaining means adapted to receive and retain the temperature sensor such that the temperature sensor is capable of being responsive to said affected temperature change when the temperature sensor is received by the sensor retaining portion. Such sensor retaining means can be a channel adjacent to the core of the absorbent article in communication with a through hole in the back sheet or the top sheet of the absorbent article through which the temperature sensor can be inserted. However, such sensor retaining means is arranged such that it will not increase the risk for leakage or inconvenience for the user.

The sensor of the kit can be a reusable sensor and the kit is not limited to one single absorbent article; instead, the kit can include a plurality of absorbent articles. Such a kit with a reusable temperature sensor is advantageous, since the same temperature sensor can be used with a plurality of absorbent articles. Thus, the kit will be cheaper than a kit with one sensor per absorbent article.

The example embodiments of the kit have similar features and advantages as the absorbent article described above, except for the temperature sensor.

Generally, all terms used in the claims are to be interpreted according to their ordinary meaning in the technical field, unless explicitly defined otherwise herein. All references to "a/an/the element, device, component, means, step, etc" are to be interpreted openly as referring to at least one instance of said element, device, component, means, step, etc., unless explicitly stated otherwise.

Other objectives, features and advantages of the present invention will appear from the following detailed disclosure, from the attached dependent claims as well as from the drawings.

BRIEF DESCRIPTION OF THE DRAWINGS

These and other aspects of the present invention will now be described in more detail, with reference to the appended drawings showing embodiment(s) of the invention, in which.

All the figures are highly schematic, not necessarily to scale, and they show only parts which are necessary in order to elucidate the invention, other parts being omitted or merely suggested.

DETAILED DESCRIPTION OF THE DRAWINGS

Herein words as upper, lower, below, above etc. are intended to have their ordinary meaning in a vertical direction, when an absorbent article is in use. Thus, an upper portion is a portion that is closer to a user than a lower portion. Further, front and back portions of the absorbent article are intended to mean portions which are at front and back, respectively, in relation to the user, when the absorbent article is in use.

Figure 1:
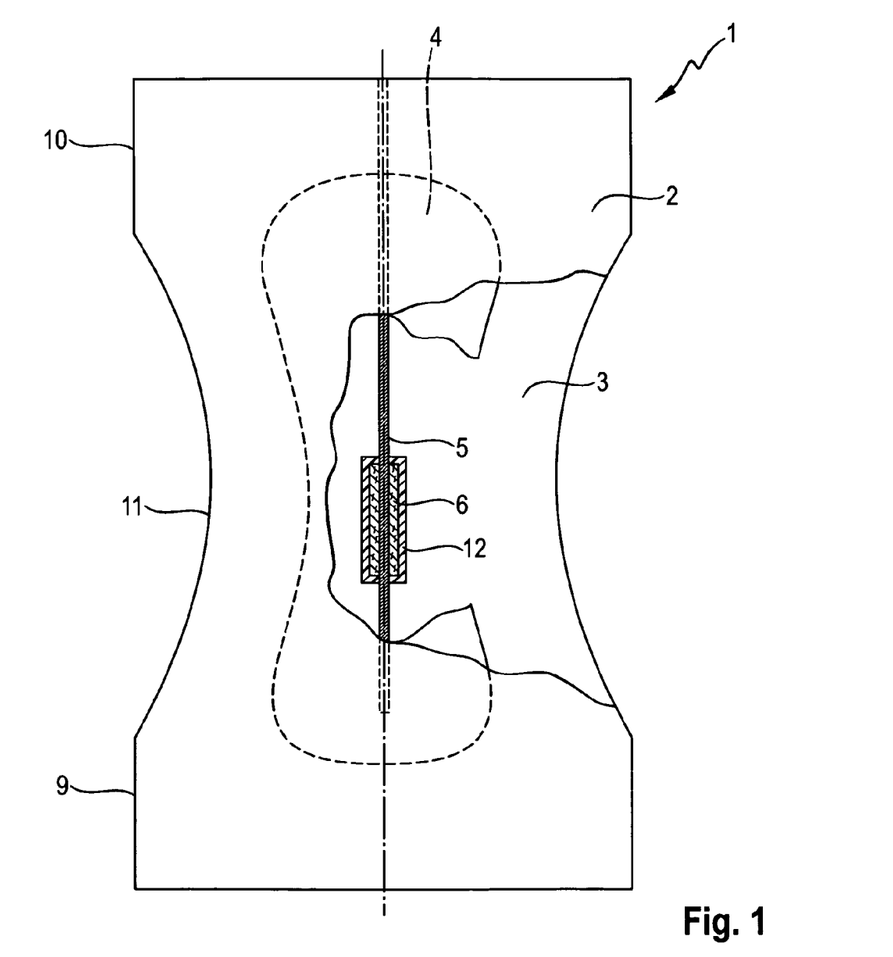
FIG. 1 is a schematic plan view of an absorbent article according to at least a first example embodiment of one aspect of the present invention.
Figure 2:
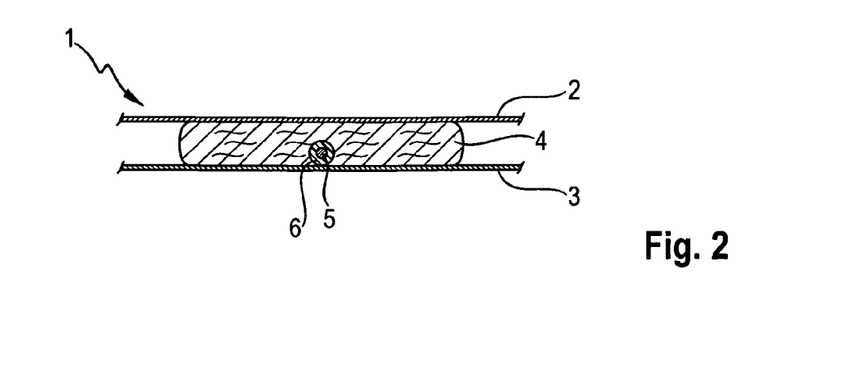
FIG. 2 is a schematic cross sectional view of the absorbent article in FIG. 1.

FIGS. 1 and 2 illustrate an absorbent article 1 according to at least one exemplary embodiment. Generally, an absorbent article includes a top sheet 2, a back sheet 3 and an absorbent core 4 arranged there between, as is illustrated by the cross-sectional view in FIG. 2. In use, the top sheet 2 is facing the crotch portion of the user and the back sheet 3 is on the opposite side of the core 4. In a longitudinal direction, an absorbent article generally includes a front portion 9, a back portion 10 and a crotch portion 11 arranged there between. In FIGS. 1 and 2 the absorbent article is shown in form of an adult incontinence product, i.e. a diaper 1. The principles of the present disclosure are, however, applicable to other absorbent articles such as baby or toddler diapers, sanitary towels or other known absorbent articles. The diaper 1, which is illustrated in FIGS. 1 and 2, is an example of a conventional diaper except for the presence of a temperature sensor 5 and a temperature change material 6.

The temperature sensor is herein exemplified as a conducting thread thermometer 5, generating an electronic signal as a response to a temperature change. The conducting thread thermometer 5 is arranged substantially lengthwise along the diaper 1, that is, such that the longitudinal extension of the conducting thread thermometer 5 substantially coincides with the longitudinal direction of the diaper 1. Suitably, the conducting thread thermometer 5 extends along a portion of the longitudinal direction of the core 4 expected to be wetted by the supply of excrement, and especially urine. Thus, the diaper can be cheaper to produce compared to a diaper having a conducting thread thermometer 5 along the entire longitudinal extension of the core 4. However, the conducting thread thermometer 5 can alternatively extend along another portion of the core 4 or along the entire longitudinal extension of the core 4. Further, the conducting thread thermometer 5 is arranged adjacent to the back sheet 3 below the core 4 of the diaper 1. A conducting thread thermometer 5 arranged near the back sheet 3 side of the core 4 is advantageous. The conducting thread thermometer 5 can be glued or sewn into the diaper 1.

In FIGS. 1 and 2, temperature change material 6 is coated on a portion of the conducting thread thermometer 5 located in the crotch portion 11 of the diaper 1. Such a position of the temperature change material 6 allows for detection of smaller amounts of supply of excrement. If greater amounts of excrement are to be detected, the temperature change material can be arranged nearer a front 9 or a back 10 portion of the diaper 1. By arranging the conducting thread thermometer 5 and temperature change material 6 inside the diaper 1 below the core 4, discrimination between feces and urine is facilitated, since the liquid of urine coming in contact with the temperature change material 6 will result in activation of the temperature change material, while the liquid of feces will be absorbed by the core 4 instead of reaching and activating the temperature change material 6. Thus, the liquid of feces will not activate the temperature change material 6.

In FIGS. 1 and 2, the temperature change material 6 is encapsulated within a water soluble polymer 12, such as alginate, or polyvinyl alcohol (pvoh). Such material protects the temperature change material 6 against humidity during storage of the absorbent articles. Instead of totally encapsulating the temperature change material 6, the temperature change material 6 can be partly covered by the water soluble polymer 12. Alternatively, the temperature change material 6 can be partly covered by the water soluble polymer 12 and another water impermeable material as long as a part of the encapsulation is water soluble such that the water of the excrement can come in contact with the temperature change material 6.

The temperature change material 6 can be an endothermic or an exothermic material, or a combination of several endothermic and/or exothermic materials. Further, instead of coating all the portions of the conducting thread thermometers 5 with one material, each portion of the conducting thread thermometer 5 can be coated with different or different types of temperature change materials 6. Thus, one portion of conducting thread thermometer 5 can be coated with an exothermic material, while another portion can be coated with an endothermic material. Still alternatively, the temperature change material 6 can be a mixture of an endothermic and an exothermic material, if it is suitable. In case of an exothermic material, the temperature increase will be greater than without an exothermic material. On the contrary, in case of an endothermic material, the temperature change will instead be a temperature decrease. Suitable materials are chemicals which are activated by liquid or water in some way, such as:

chemicals which respond to water, such as a metal hydroxide, an iron compound, acids, bases, etc.; mixtures of chemicals which react when dissolved, such as a weak acid and a base, especially citric acid and sodium bicarbonate; metal chlorides, such as magnesium chloride, potassium chloride, or calcium chloride; and/or ammonium salts, such as ammonium chloride.

The amount of temperature change material 6 is such that a detectable increase or decrease of temperature change is obtained. In case of an exothermic material, the amount of material is such that an enthalpy increase, $\Delta H$, of $\pm(0.1\text{-}150)$ J, or $\pm(0.4\text{-}50)$ J, is obtained at each supply of excrement. For instance, for calcium chloride, $CaCl_2$ a quantity of about 0.5 g can be suitable. For multiple supplies of excrement, the amount of temperature change material is multiplied such that the obtained temperature increase is multiplied by the number of supplies of excrement to be detected. That is, for two excrements, the amount is such that the total obtained enthalpy increase is (0.2-300) J, or (0.8-100) J. In case of an endothermic material, the amount of material is such that the enthalpy change is decreased by $\pm(0.1\text{-}500)$ J, $\pm(0.4\text{-}400)$ J, or $\pm(1\text{-}250)$ J at each supply of excrement. For multiple supplies of excrement, the amount of endothermic material corresponds to the desired temperature decrease multiplied by the amount of desired detectable supplies of excrement, similarly to the case with exothermic material.

The suitable amount temperature change material 6 can also be expressed in terms of the resulting temperature change. Suitably, the amount of an exothermic temperature change material corresponds to a positive temperature change, $\Delta T$, when activated by water, of at least $2°$ C., at least $5°$ C., or at least $10°$ C. For avoiding a risk that a user of the absorbent article feels a burning sensation, the positive temperature change, $\Delta T$, is not greater than $20°$ C. That is, the positive temperature change, $\Delta T$, is 2-20° C., 5-20° C., or 10-20° C. Suitably, the amount of an endothermic temperature change material 6 corresponds to at least a detectable negative temperature change, $\Delta T$, when activated by water. The temperature change, $\Delta T$, includes the temperature change due to the presence of the temperature change material and a temperature change due to a supply of excrement, $\Delta t$. The temperature change $\Delta T$ equals to a factor, C, times said temperature change due to a supply of excrement, $C*\Delta t$, wherein C is either a positive or negative. For an endothermic material temperature change material the factor C is negative. Further, for an exothermic material temperature change material the factor C is positive.

Instead of coating the conducting thread thermometer 5 with temperature change material 6, the temperature change material 6 can be held in close contact with the conducting thread thermometer 5 by a sheet of material, such as tissue or nonwoven folded or wrapped around the conducting thread thermometer 5 sandwiched between the layers of temperature change material 6. Still alternatively, the temperature change material 5 can be arranged along at least one side of the conducting thread thermometer 5.

Alternatively, instead of a conducting thread thermometer 5, any type of wire or thread which conducts electricity can be used as a temperature sensor. Generally, such a wire includes metal, however a bearer thread having carbon particles can also be used.

Instead of being arranged adjacent to the back sheet 3, the temperature sensor 5 in form of a conducting thread thermometer or alternative embodiments can be arranged anywhere in the diaper as long as it will be able to be wetted by excrement. However, it can be advantageous, if the temperature sensor 5 is not in direct contact with the skin of the wearer of the diaper 1. Therefore, the temperature sensor can be arranged vertically anywhere between the top sheet 2 and the back sheet 3, such as below the top sheet 2. If the temperature sensor is positioned in a portion of the core 4 which is near the top sheet 2, supply of a smaller amount of excrement can be detected compared to if the temperature sensor is arranged in a portion of the core 4 which is near the back sheet 3. Further, the conducting thread thermometer 5 can alternatively be arranged beneath the top sheet 2, which will increase the chances of detecting feces, since in such a case the liquid of feces can activate the temperature change material 6 before it is absorbed by the core 4 below the temperature change material 6.

Instead of coating one portion of the conducting thread thermometer 5, which is an example of a temperature sensor 5, with the temperature change material 6, the temperature change material 6 can be arranged along the entire length of the conducting thread thermometer 5, or along discrete portions of the conducting thread thermometer 5. Such discrete portions form detection zones along the conducting thread thermometer 5 for detecting multiple supplies of excrement. The number of supplies of excrement that can be detected corresponds to the number of discrete portions of temperature change material 6. Suitably, the absorbent article includes two, three, four, five or another arbitrary number of discrete portions of temperature change material 6. Suitably, the distance between two adjacent discrete portions is 1-20 cm, the distance is 2-10 cm, or 2-6 cm. In case of a plurality of discrete portions of temperature change material 6 in form of exothermic material, the amount of temperature change material 6 at each portion is such that an enthalpy increase of 0.1-150 J, or 0.4-50 J, is obtained at each supply of excrement. If, for instance, three supplies of excrement are to be detected, the amount of material corresponds to a total enthalpy increase of 10.3-450 J, or 1.2-150 J, applied over three portions of the conducting thread thermometer 5. If the temperature change material 6 is arranged along the entire length of the conducting thread thermometer 5, the amount of temperature change material 6 needed for detecting multiple supplies of excrement is higher than in case of discrete portions.

Instead of using a conducting thread thermometer 5, the temperature sensor can be conductive ink including carbon, silver, platinum or other conductive particles, printed on a substrate or carrier material, such as paper, nonwoven, plastic sheet. In such a case, temperature change material can be printed adjacent to the printed temperature sensor 5 in a desired pattern, such as oblong paths, discrete circles, ellipses. Further, above the base material and the temperature change material 6 a water soluble polymer covering the temperature change material 6 can be arranged. Such a cover protects, as the encapsulation of the embodiment in FIG. 1, the temperature change material 6 against moisture during storage. Such a temperature sensor can be arranged in the absorbent article during the manufacturing process. During the manufacturing process, the temperature sensor 5 can suitably be arranged below the core 4 on the side of the back sheet 3 adjacent to the core, in an arbitrary layer above the core 4 and below the top sheet 2, or outside (i.e. on the side facing away from the core 4) the back sheet 3, if the back sheet 3 allows the water of the excrement to come into contact with the temperature sensor 5. Alternatively, a user or another person can arrange such a temperature sensor above the top sheet 2 before use.

Suitably, a short edge of such a carrier material is formed for being able to be detachable to or to receive a reusable processing/reader unit for collecting data. Such a processing/reader unit can also analyse the data.

Still alternatively, the temperature change material can be arranged adjacent to the back sheet 3 below the core 4 of the diaper 1, while the temperature sensor 5 can be arranged outside the back sheet 3. In such a case, the back sheet 3 suitably includes an indication, for instance in form of print or holes, for the correct position of the temperature sensor 5, for ensuring that the temperature sensor will be arranged such that it is capable of being responsive to the temperature change affected by the temperature change material.

According to an alternative embodiment, not shown in the figures, the absorbent article in form of a diaper includes the temperature change material and an opening in the top sheet or back sheet through which a reusable temperature sensor is inserted such that it will be in contact with the core. Further, the diaper can include a channel or similar in communication with the through hole into which the temperature sensor is inserted. Alternatively, such a reusable temperature sensor can alternatively be inserted into a pocket or similar on the back sheet or top sheet of the diaper. Still alternatively, the reusable temperature sensor can be attached to the back sheet or top sheet using suitable fastening means, such as an adhesive. In such a case, the top sheet or back sheet suitably includes an indication, for instance in form of print, for the correct position of the temperature sensor, for ensuring that the temperature sensor will be arranged such that it is capable of being responsive to the temperature change affected by the temperature change material. Further, the amount of temperature change material is such that the temperature sensor is capable of being responsive to the affected temperature change through the back sheet or top sheet of the diaper, respectively. Generally, such a reusable temperature sensor can be provided separately or as a part of a kit with a diaper, or a plurality of diapers.

Even if the diaper 1 in FIGS. 1 and 2 includes a single conducting thread thermometer 5, the claims are not limited to a single conducting thread thermometer 5. Arranging a plurality conducting thread thermometers 5 in the diaper 1, allows for an alternative way of detecting multiple supplies of excrement. Further, instead of coating all of the conducting thread thermometers 5 with one material, each of the conducting thread thermometers 5 can be coated with different or different types of temperature change materials 6. Thus, one of the conducting thread thermometers 5 can be coated with an exothermic material, while another one of the conducting thread thermometers 5 can be coated with an endothermic material.

Alternatively, the temperature sensor 5 can be any other type of temperature sensor, for example a liquid crystal thermometer that changes colour to indicate different temperatures. Such a sticker gives a visual signal, in form of the colour change, instead of an electronic response. Still alternatively, the temperature sensor 5 can give a permanent visual indication if the temperature has exceeded a predetermined threshold value.

Still alternatively, before being arranged in the diaper 1 the temperature change material 6 can suitably be enclosed by a water impermeable housing including through holes. The through holes of such housing allow only a limited amount of water of excrement to come in contact with the temperature change material 6. Consequently, less water of excrement is will activate the temperature change material 6. Therefore, less temperature change material 6 is needed.

Figure 3:
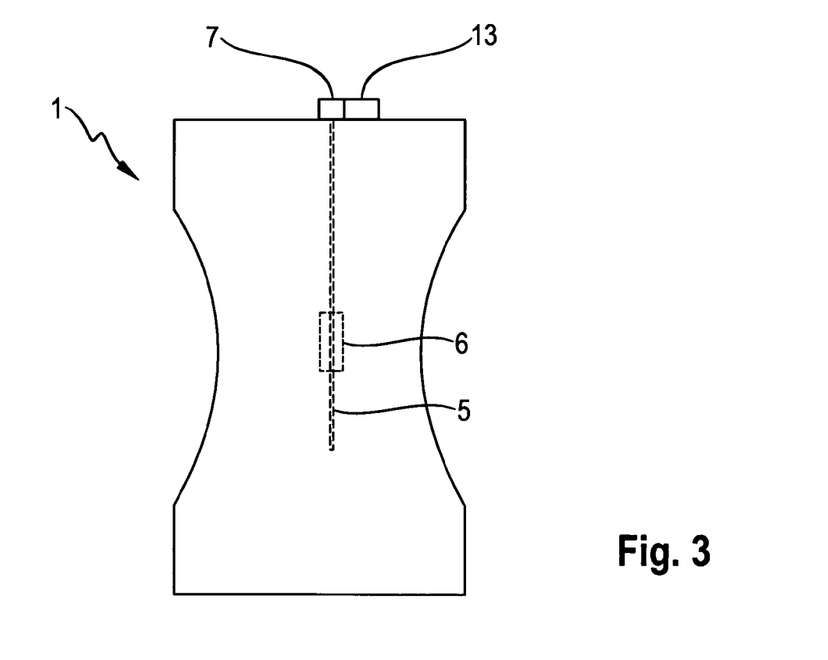
FIG. 3 illustrates a system for detecting a supply of excrement according to at least a first example embodiment of the present invention.

FIG. 3 illustrates a system for detecting a supply of excrement. The system includes an absorbent article, herein exemplified as the diaper 1 illustrated in FIGS. 1 and 2, and a processing unit 8, arranged separate from said absorbent article 1. The conducting thread thermometer 5, which is an example of a temperature sensor, is connected to a reader unit 7. The reader unit 7 measures the resistance in the thread and converts the measured resistance into an electronic signal representative of the temperature in the core 4. A transmitter 13 connected to the reader unit 7 transmits the signal to a receiver 14 connected to the processing unit 8. Suitably, the reader unit 7 and the transmitter 13 are reusable, attachable to and detachable from the absorbent article. In the embodiment shown in FIG. 3, the processing unit 8 is arranged separate from the diaper 1 in a computer 15 including a display unit 16. The computer 15 can be, for instance, a personal computer or a hand-held computer.

The processing unit 8 includes a microcomputer and software for performing data analysis. Further, the processing unit 8 is adapted to detect a supply of excrement, indicate a supply of excrement, and, suitably, discriminate a supply of urine and a supply of feces. The indication can be any form of notification, such as an alarm or a note in a report.

Alternatively, the processing unit 8 can be arranged in a cell phone, or integrated in or on the absorbent article 1. Still alternatively, a processing unit 8 attached to the diaper 1 can include the reader unit 7 and can be adapted to analyse, detect, and indicate a supply of excrement. In a still alternative embodiment, indication of a supply of excrement is handled by a separate alarm unit.

Figure 4:
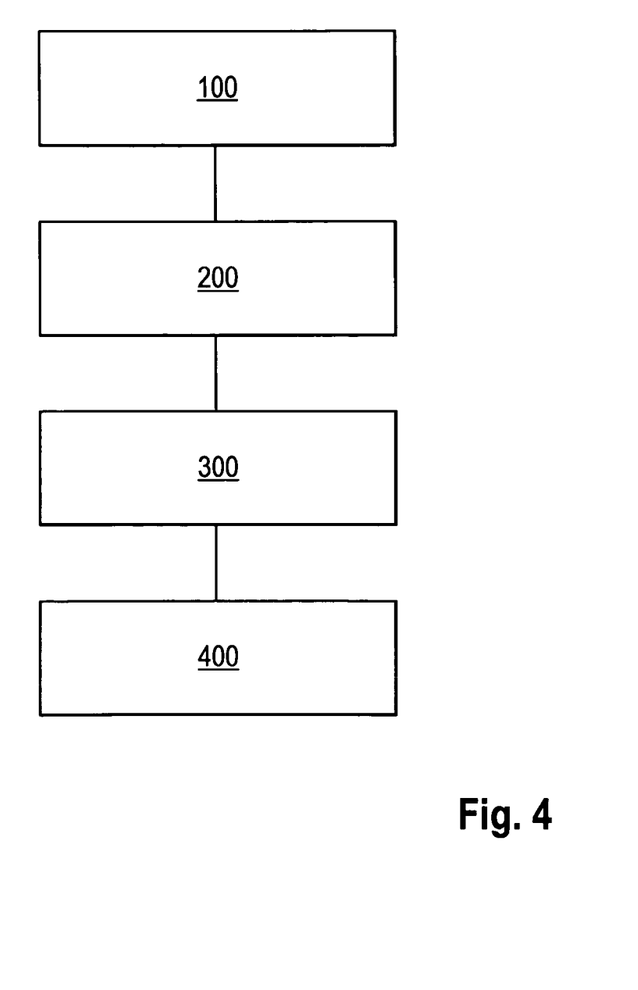
FIG. 4 illustrates a method for detecting a supply of excrement according to at least a first example embodiment of the present invention.

FIG. 4 illustrates a method for detecting a supply of excrement into an absorbent article 1. The method includes the steps of:
  determining 100 a change of temperature, wherein the change of temperature is affected by the temperature change material; and
  detecting 200 a supply of excrement based on the change of temperature.

The change of temperature, $\Delta T$, affected by the temperature change material can be expressed as a sum of a part describing the change of temperature due to the supply of excrement, $\Delta t$, and one part describing temperature change affected by the temperature change material, $\Delta t_a$. That is, $\Delta T = \Delta t + \Delta t_a$. Alternatively, the change of temperature, $\Delta T$, affected by the temperature change material can be expressed as $\Delta T = C * \Delta t$, where C is a factor depending on the amount of temperature change material. If the temperature change material is exothermic, C is a positive factor, and if the temperature change material is endothermic, C is a negative factor.

Further, the method can include the step of indicating 300 a supply of excrement and the step of discriminating 400 between a supply of excrement in form of urine and a supply of excrement in form of feces. In certain embodiments, if the temperature change material is an endothermic material, a supply of excrement in form of urine is associated with a decrease in temperature while a supply of excrement in form of feces is associated with an increase in temperature. If the temperature change material is an exothermic material, a supply of excrement in form of urine is associated with at least a 1.5 times greater change of temperature per unit time than a supply of excrement in form of feces. Alternatively, if the temperature change material is an exothermic material, a supply of excrement in form of urine is associated with a 5 times, alternatively 3 times, and still alternatively 1.5 times greater change of temperature per unit time than a supply of excrement in form of feces. The step of discriminating between a supply of excrement in form of urine and a supply of excrement in form of feces requires sophisticated signal processing.

The disclosure relates also to a kit including an absorbent article and a separate temperature sensor (not shown). In one exemplary embodiment, the absorbent article includes a channel or recess in, or adjacent to, the core adjacent to the back sheet and in communication with a through hole in the back sheet, which is an example of sensor retaining means. The channel is at least partly surrounded by a temperature change material. The size of the channel is slightly greater than the size of the temperature sensor. Thus, the temperature sensor can be inserted into the channel through the through hole for being arranged adjacent to the temperature change material and will therefore be capable of being responsive to a temperature change affected by the temperature change material. Suitably, the through hole is arranged in a portion of the absorbent article, which is not expected to be wetted in normal use, and covered by liquid impermeable cover for decreasing the risk of leakage of the absorbent article due to the through hole. Further, the sensor retaining means is arranged such that it will not increase the risk for leakage or inconvenience for the user. The channel described above can also be an example of a sensor retaining portion related to the absorbent article including a reusable temperature sensor.

The sensor of the kit can be a reusable sensor and the kit is not limited to one single absorbent article; instead, the kit can include a plurality of absorbent articles. Such a kit with a reusable temperature sensor is advantageous, since the same temperature sensor can be used with a plurality of absorbent articles. Thus, the kit will be cheaper than a kit with one sensor per absorbent article.

EXPERIMENTS

Figure 5:
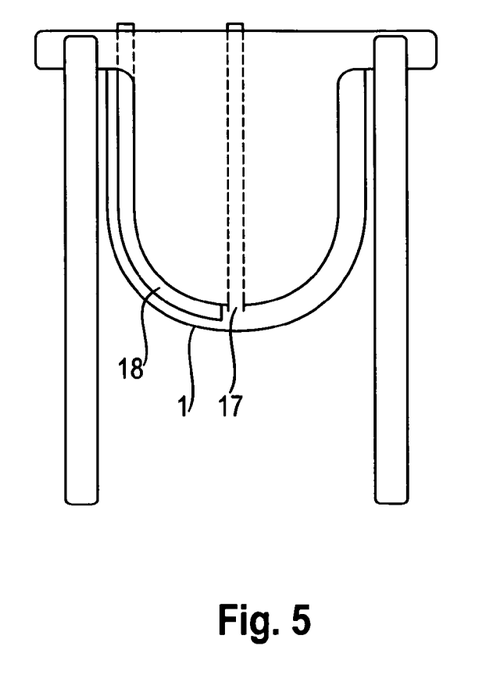
FIG. 5 illustrates experimental equipment for experimental measurements for an embodiment according to the invention.

FIG. 5 illustrates experimental equipment for experimental measurements for an absorbent article, here, in form of a diaper 1. The experimental equipment 20 includes a body like bowl 19 made of Plexiglas. The body like bowl 19 is filled with water from an ordinary tap. The water in the body like bowl 19 is heated by a heater (not shown) connected to the body like bowl 19 by a tube (not shown). The water circulates from the heater to the body like bowl 19 and the heater is adjusted to give the water a temperature of 37° C. The body like bowl filled with water is used to simulate a lower part of the body of a user on which an absorbent article is arranged.

Figure 6:
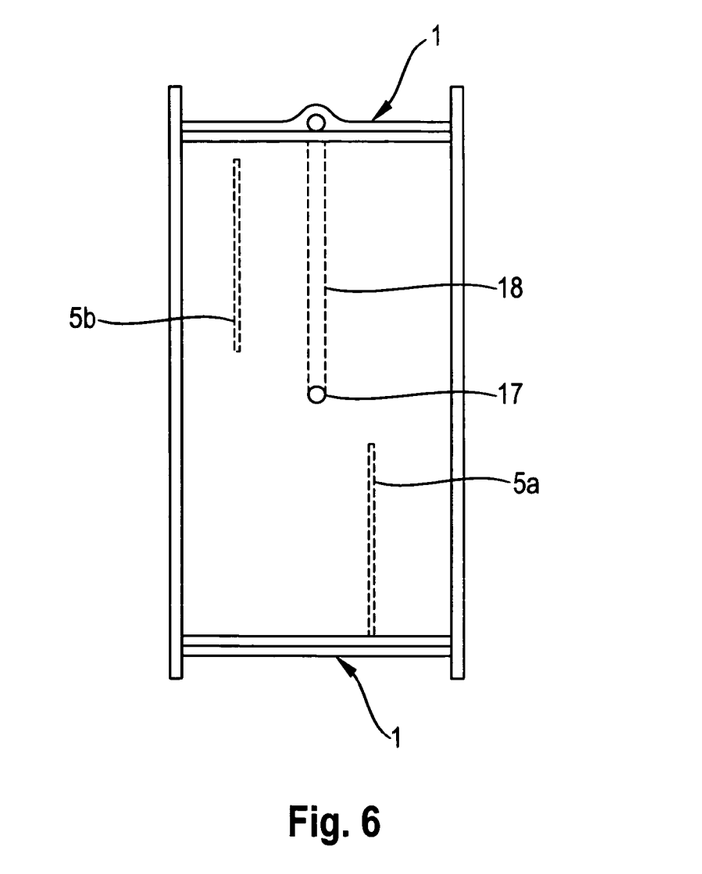
FIG. 6 illustrates an absorbent article and a portion of the experimental equipment according to FIG. 5 for illustrating the positions of the temperature sensors during experiments.

With reference to FIG. 6, the diaper used in the experiments was an adult incontinence diaper called TENA® Flex Super Medium provided by SCA Hygiene Products AB. The temperature change material 6 was arranged in the vicinity of the temperature change sensor 5a. In detail, the temperature change material 6 was arranged around the measuring part of the temperature sensor 5a. Thereafter, a filter paper was arranged around the measuring part of the temperature sensor 5a and the temperature change material 6 such that the temperature change material 6 was retained in place. The filter paper was fixated on the temperature sensor 5a using a tape. During the experiments an additional temperature sensor 5b, without any temperature change material arranged adjacent to it, was arranged in the diaper as a reference temperature sensor 5b. FIG. 6 illustrates also the positions of the temperature sensors 5a, 5b in the experimental setup according to FIG. 5. The measuring parts of both the coated temperature sensor 5a and the reference temperature sensor 16 were arranged in the crotch region of the diaper 1 on opposite sides at equal distances of a urine supply tube 17 as well as a feces supply tube 18 well within the zone wetted by the supplied artificial urine. Both temperature sensors 5a, 5b were arranged below the core 4 on the back sheet 3, according to FIG. 2, through corresponding holes in the back sheet 3. The holes around the cables of the temperature sensors 5a, 5b were sealed using tape. The temperature sensors 5a, 5b used during the experiments were conventional temperature sensors 5a, 5b having a measurement range from −10° C. to +58° C. provided by MSR Electronics, GmbH Oberwierstrasse 16, CH-8444 Henggart, Switzerland. However, the temperature sensors 5a, 5b could be of any other suitable known type. For collecting data a data collector called MSR 145W provided by the same company was used. The temperature sensors 5a, 5b were connected to a computer and software called MSR from MSR Electronics was used to collect data.

The experiments were conducted in a climate room with following specifications: 23±1° C. and 50±10% RH.

During the experiments an artificial urine solution (SUB) was used. Any of the available recipes known by a person skilled in the art could be used. In particular, a 0.9% NaCl solution could be used. For each experiment 200 ml artificial urine was measured and poured into a beaker, which was placed on a laboratory hot plate with magnetic stirrer and heated. In such a way, the temperature of the water in the beaker was substantially equal. During heating, the temperature was measured using a thermometer and the artificial urine was heated to 37° C.

During experiments, sausage was used as artificial feces. The sausage was put in a plastic bag with weights and sealed. The plastic bag with sausage was arranged in a beaker with water, which was placed on a laboratory hot plate with magnetic stirrer and heated. In such a way, the temperature of the water in the beaker was substantially equal. For the third experiment, 100 g sausage was heated to 37° C. and the temperature of the sausage was controlled using a thermometer before supplying it to the diaper.

Before each experiment, the diaper with temperature sensors 5a, 5b were arranged around the body like bowl 19 tightly, such that the front and back parts of the upper end of the diaper 1 was on equal heights, and with standing gathers on the outside of the diaper. For ensuring that the diaper 1 will stay in place during the experiment, the diaper 1 was secured with tape against the outside of the body like bowl at its upper end. The mouths of the urine supply tube 17 as well as a feces supply tube 18 were covered by caps. Before the experiment was started the temperature of diaper was allowed to stabilise.

The experimental approach was as follows. When the diaper 1 was arranged on the bowl 19, the data collection was started. When the temperature had stabilised, after approximately 30 minutes, artificial urine or artificial feces having desired temperature, i.e. 37° C. was supplied to the diaper. The artificial urine was supplied using a funnel via the urine supply tube 17. After supply of artificial urine the urine supply tube 17 was covered by a cap, such that the heat of the artificial urine could not dissipate through the urine supply tube 17. The artificial feces were supplied using the feces supply tube 18 using a slightly bent rod being thicker in the end which is used to push the artificial feces. After supply of artificial feces, the feces supply tube 18 was covered by a cap, such that the heat of the artificial urine could not dissipate through the feces supply tube 18.

Experiment 1

Figure 7:
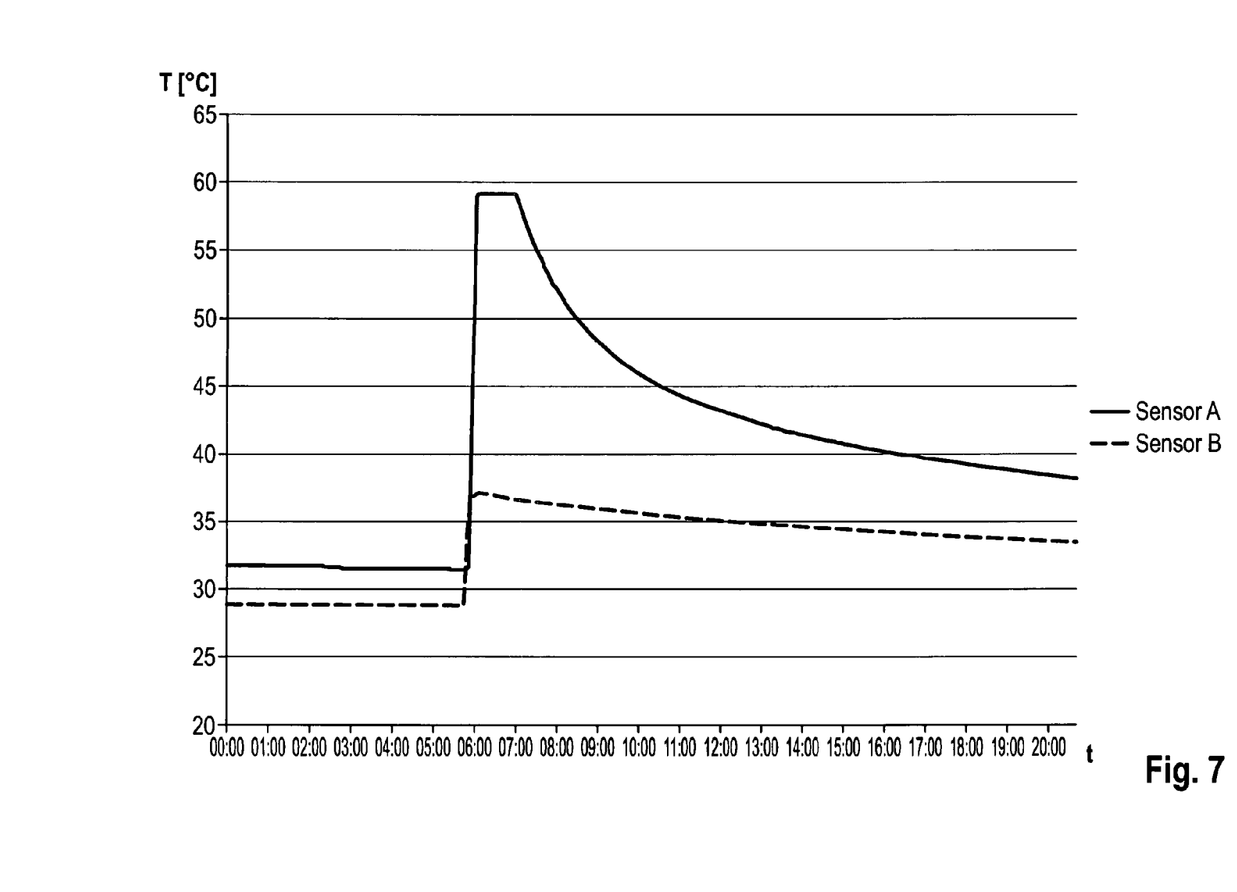
FIG. 7 is measurement data obtained for one embodiment of the invention using the experimental setup in FIGS. 5 and 6.

FIG. 7 is measurement data obtained during a first experiment using the experimental setup in FIGS. 5 and 6. During this experiment, the temperature change material comprised an exothermic material in form of 0.35 grams of Magnesium Chloride was arranged adjacent the temperature sensor 5a called sensor A in the graph. Sensor B is a reference temperature sensor 5b without temperature change material. The sensor signal from both sensors is initially stable at approximately 32° C. (sensor A) and 29° C. (sensor B), respectively. When excrement, in form of artificial urine, see above, is supplied to the diaper the temperature increases quickly. It is clear from FIG. 7 that the measured total change of temperature when excrement is supplied into the diaper is greater for sensor A with exothermic material arranged adjacently, than the measured change of temperature for sensor B without the exothermic material. The change of the temperature signal, $\Delta T$ of sensor A is approximately 27° C. and the corresponding change of temperature $\Delta t$ for sensor B is approximately 8° C. Further, the temperature decay is remarkably faster for sensor A than for sensor B. By arranging 0.35 grams of Magnesium Chloride adjacent to the temperature sensor, the change of temperature is amplified at least by a factor 3. That is $\Delta T \approx 3 * \Delta t$. The measured total change of temperature of sensor A, $\Delta T$, can be divided into one part corresponding to the increase due to the supply of excrement, $\Delta t$, and one part due to the influence of the temperature difference due to the temperature change material, $\Delta t_a$. That is, $\Delta T = \Delta t + \Delta t_a$. In such a case the influence $\Delta t_a$ is approximately 19° C.

Experiment 2

Figure 8:
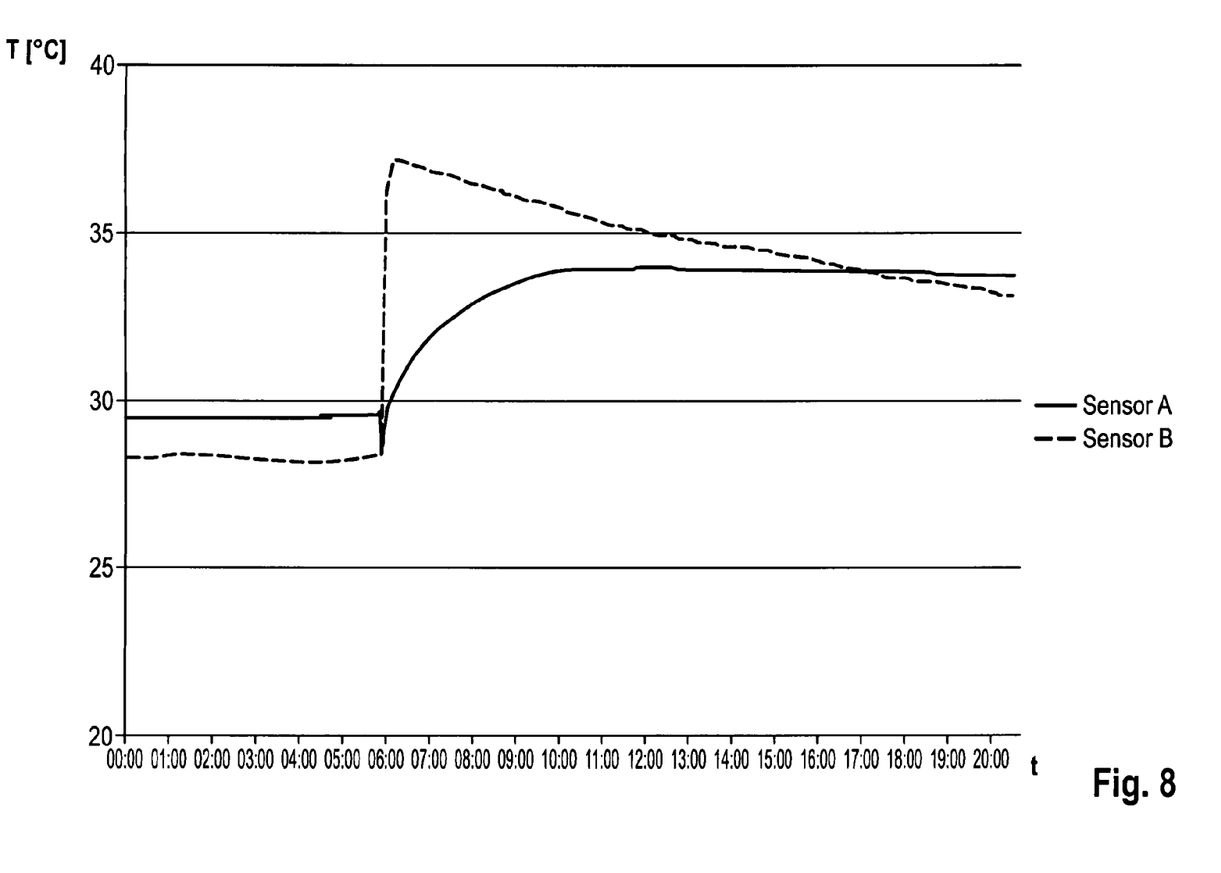
FIG. 8 is measurement data obtained for one embodiment of the invention using the experimental setup in FIGS. 5 and 6.

FIG. 8 is measurement data obtained during a second experiment using the experimental setup in FIGS. 5 and 6. During this experiment, the temperature change material comprised an endothermic material in form of 0.6 grams of a mixture including 50 weight % citric acid and 50 weight % sodium bicarbonate, $NaHCO_3$, was arranged adjacent the temperature sensor 5a called sensor A in the graph. Sensor B is a reference temperature sensor 5b without temperature change material. The sensor signal from both temperature sensors 5a, 5b is initially stable at approximately 29° C. (sensor A) and 27° C. (sensor B), respectively. When excrement, in form of artificial urine, see above, is supplied to the diaper the temperature measured by sensor A, having endothermic material arranged adjacently, decreases quickly and there is a dip in the curve before the temperature increases. On the contrary, the temperature measured by sensor B increases quickly. The change of the temperature signal, $\Delta T$ of sensor A is approximately −1.5° C. and the corresponding change of temperature $\Delta t$ for sensor B is approximately 10° C. Further, while the temperature measured by sensor B decreases after the peak value, the temperature measured by sensor A increases after the bottom value. By arranging 0.6 grams of a mixture including 50 weight % citric acid and 50 weight % sodium bicarbonate adjacent to the temperature sensor, the change of temperature is affected to decrease approximately by a factor −0.15 instead of to increase due to supply of artificial urine. That is, $\Delta T \approx -0.15 * \Delta t$. In other words, the factor C is negative and equals −0.15. The measured total change of temperature of sensor A, $\Delta T$, can as is explained above, be divided into one part corresponding to the increase due to the supply of excrement, $\Delta t$, and one part due to the influence on the change of temperature due to the temperature change material, $\Delta t_a$. That is, $\Delta T = \Delta t + \Delta t_a$. However, since the temperature decrease due to the endothermic material has to counteract the increase due to a supply of excrement, the actual negative change of temperature at sensor A due to the endothermic material, $\Delta t_a$, is $\Delta T - \Delta t = -11.5°$ C.

Experiment 3

Figure 9:
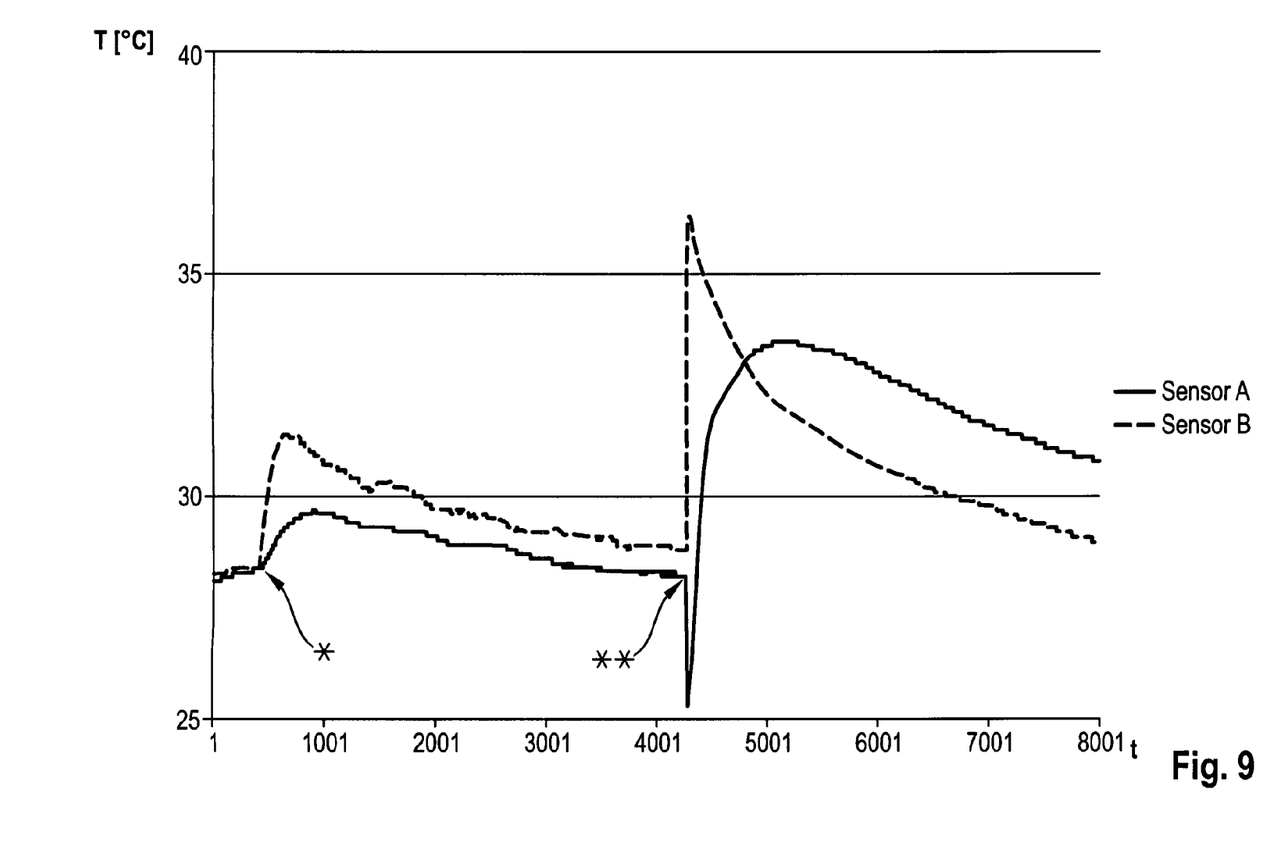
FIG. 9 is measurement data obtained for one embodiment of the invention using the experimental setup in FIGS. 5 and 6.

FIG. 9 is measurement data obtained during a third experiment using the experimental setup in FIGS. 5 and 6. During this experiment, the temperature change material comprised an endothermic material in form of 0.6 grams of a mixture including 50 weight % citric acid and 50 weight % sodium bicarbonate was arranged adjacent the temperature sensor called sensor A in the graph. Sensor B is a reference sensor without temperature change material. The sensor signal from both sensors is initially stable at approximately 28.5° C. (sensor A) and 28.5° C. (sensor B), respectively. When excrement, in form of artificial feces indicated by *, see above, is supplied to the diaper the temperature measured by sensor A having endothermic material arranged adjacently increases slightly. Also, the temperature measured by sensor B increases. The response of the sensors A and B to artificial feces are substantially similar. It is believed that the small difference in response measured is due to small differences in how the artificial feces exit the supply tube relative to the position of the sensors A and B. In this case, the presence of endothermic material does not affect $\Delta T$, since the endothermic material will not come into contact with the water of the artificial feces due to its vertical position in the diaper 1.

After the temperature increase due to supply of artificial feces, the measured temperature returns to equilibrium. When excrement, in form of artificial urine indicated by **, is supplied to the diaper the temperature measured by sensor A, having endothermic material arranged adjacently, decreases quickly and there is a dip in the curve before the temperature increases. On the contrary, the temperature measured by sensor B increases quickly. The difference of the temperature signal, $\Delta T_u$ of sensor A is approximately −3° C. and the corresponding temperature difference $\Delta t_u$ for sensor B is approximately 8° C. Further, while the temperature measured by sensor B decreases after supply of artificial urine, the temperature measured by sensor A increases. By arranging 0.6 grams of a mixture including 50 weight % citric acid and 50 weight % sodium bicarbonate adjacent to the temperature sensor, the temperature difference is affected to decrease approximately by a factor −0.375 instead of to increase. That is $\Delta T_u \approx -0.375 * \Delta t_u$. The measured total temperature difference of sensor A, $\Delta T_u$, can as is explained above, be divided into one part corresponding to the increase due to the supply of artificial urine, $\Delta t_u$, and one part due to the influence of the temperature difference due to the temperature change material, $\Delta t_{ua}$. That is, $\Delta T_u = \Delta t_{ua} + \Delta t_a$. However, since the temperature decrease due to the endothermic material has to counteract the increase due to supply of artificial urine, the actual negative temperature difference at sensor A due to the endothermic material, $\Delta t_{ua}$, is $\Delta T_u - \Delta t_u = -11°$ C.

Even though the invention has been described with reference to specific exemplifying embodiments thereof, many different alterations, modifications and the like will become apparent for those skilled in the art. For example, additionally, variations to the disclosed embodiments can be understood and effected by the skilled addressee in practicing the claimed invention, from a study of the drawings, the disclosure, and the appended claims. In the claims, the word "comprising" does not exclude other elements or steps, and the indefinite article "a" or "an" does not exclude a plurality. A single unit may fulfill the functions of several items recited in the claims. The mere fact that certain measures are recited in mutually different dependent claims does not indicate that a combination of these measured cannot be used to advantage.

The invention claimed is:

1. An absorbent article comprising:
    a temperature sensor;
    a temperature sensor retaining portion configured to retain the temperature sensor within the absorbent article; and
    at least one temperature change material arranged such that it is capable of affecting a temperature change due to a supply of excrement, and such that said temperature sensor is capable of providing an electronic response to said affected temperature change.

2. The absorbent article according to claim 1, wherein said temperature change material is arranged adjacent to the temperature sensor.

3. The absorbent article according to claim 1, wherein a distance between the temperature sensor and the temperature change material is 0-10 mm.

4. The absorbent article according to claim 1, wherein said temperature change material is arranged in physical contact with at least a portion of said temperature sensor.

5. The absorbent article according to claim 1, wherein said temperature sensor is reusable in additional absorbent articles and arrangeable in said absorbent article such that said temperature sensor is capable of being responsive to said affected temperature change.

6. The absorbent article according to claim 5, wherein said sensor retaining portion is arranged such that a temperature sensor inserted into said sensor retaining portion is capable of being responsive to said affected temperature change.

7. The absorbent article according to claim 1, wherein said temperature change material is arranged in at least two discrete portions spaced apart from each other.

8. The absorbent article according to claim 1, wherein said absorbent article comprises a back sheet, a top sheet and an absorbent core arranged between the back sheet and the top sheet, wherein the temperature sensor and the temperature change material are arranged adjacent to the back sheet of the absorbent article in contact with the absorbent core, wherein said temperature sensor is arranged substantially longitudinally along the absorbent article.

9. The absorbent article according to claim 1, wherein said temperature change material is at least partly covered by a water soluble polymer.

10. The absorbent article according to claim 1, wherein said temperature sensor and said temperature change material are arranged on a carrier material.

11. The absorbent article according to claim 1, wherein an amount of said temperature change material is sufficient to affect a change in enthalpy, $\Delta H$, of $\pm(0.1\text{-}500)$ J, for each supply of excrement.

12. The absorbent article according to claim 1, wherein said affected temperature change, $\Delta T$, is equal to a factor, C, times a temperature change due to a supply of excrement, $\Delta t$, that is, $C*\Delta t$, wherein C is either positive or negative.

13. The absorbent article according to claim 1, wherein said temperature change material comprises an endothermic material.

14. The absorbent article according to claim 1, wherein said temperature change material comprises an exothermic material.

15. The absorbent article according to claim 14, wherein an amount of said temperature change material is sufficient to affect a temperature change, $\Delta T$, when activated by water, of at least 2° C.

16. The absorbent article according to claim 14, wherein an amount of said temperature change material is sufficient to affect a change in enthalpy $\Delta H$, of $-(0.1\text{-}150)$ J, for each supply of excrement.

17. The absorbent article according to claim 1, wherein said temperature change material comprises a chemical which is activated in contact with water.

18. The absorbent article according to claim 1, wherein said temperature change material comprises a mixture of chemicals which react when dissolved into water.

19. The absorbent article according to claim 1, wherein said temperature change material comprises a metal chloride.

20. The absorbent article according to claim 1, wherein said temperature change material comprises an ammonium salt.

21. A system for detecting a supply of excrement into an absorbent article, said system comprising
the absorbent article according to claim 1, wherein said temperature sensor is arranged to generate an output signal representative of the temperature of said absorbent article, and
a processing unit adapted to process said output signal generated by the temperature sensor, wherein
said processing unit is adapted to
determine a change of temperature, wherein said change of temperature is affected by the temperature change material, and
detect a supply of excrement into said absorbent article based on said change of temperature, whereby the supply of excrement is associated with a change of temperature.

22. The system for detecting a supply of excrement according to claim 21, wherein said processing unit is further adapted to discriminate between a supply of excrement in form of urine and a supply of excrement in form of faeces based on said change of temperature.

23. A method of detecting a supply of excrement into an absorbent article, wherein said absorbent article is the absorbent article according to claim 1, said method comprising the steps of:
determining a change of temperature, wherein said change of temperature is affected by the temperature change material; and
detecting a supply of excrement based on said change of temperature.

24. The method of detecting a supply of excrement into an absorbent article according to claim 23, further comprising the step of discriminating between a supply of excrement in form of urine and a supply of excrement in form of faeces based on said change of temperature.

25. A kit comprising an absorbent article and a temperature sensor, wherein said absorbent article comprises a temperature sensor retaining portion configured to retain the temperature sensor within the absorbent article and at least one temperature change material arranged such that it is capable of affecting a temperature change due to a supply of excrement, and wherein said temperature sensor is capable of providing an electronic response to said affected temperature change when arranged in contact with said absorbent article.

* * * * *